United States Patent [19]

Neumeyer et al.

[11] Patent Number: 5,698,179
[45] Date of Patent: Dec. 16, 1997

[54] IODINATED NEUROPROBE FOR MAPPING MONOAMINE REUPTAKE SITES

[75] Inventors: John L. Neumeyer, Wayland; Richard A. Milius, Boston, both of Mass.; Robert B. Innis, Hamden, Conn.

[73] Assignee: Neuro Imaging Technologies, LLC, Boston, Mass.

[21] Appl. No.: 468,575

[22] Filed: Jun. 6, 1995

Related U.S. Application Data

[63] Continuation-in-part of Ser. No. 185,689, Jan. 24, 1994, Pat. No. 5,439,666, which is a continuation of Ser. No. 841,617, Feb. 25, 1992, Pat. No. 5,310,912.

[51] Int. Cl.$^6$ .................... A61K 51/04; A01N 43/42; C07D 451/02
[52] U.S. Cl. .................. 424/1.85; 424/1.81; 514/304; 546/124
[58] Field of Search .................. 424/1.85, 1.81; 514/304; 546/124

[56] References Cited

U.S. PATENT DOCUMENTS

| | | | |
|---|---|---|---|
| 3,813,404 | 5/1974 | Clarke et al. | 260/292 |
| 4,794,178 | 12/1988 | Coenen et al. | 536/122 |
| 4,942,231 | 7/1990 | Mertens | 540/586 |
| 5,098,996 | 3/1992 | Jacobson et al. | 530/303 |
| 5,104,638 | 4/1992 | Nosco | 424/1.1 |
| 5,128,118 | 7/1992 | Carroll et al. | 424/1.1 |
| 5,186,921 | 2/1993 | Kung et al. | 424/1.1 |
| 5,200,169 | 4/1993 | Wilbur et al. | 424/1.1 |
| 5,369,113 | 11/1994 | Moldt et al. | 514/304 |

OTHER PUBLICATIONS

"Abstracts of Panels and Posters", American College of Neuropsychopharmacology, 29th Annual Meeting, 1990.
Boja et al., "New, Potent Cocaine Analogs: Ligand Binding and . . . ", Europ. J. of Pharm. 184:329–332, 1990.
Boja et al., "[$^{125}$I]RTI–55: A Potent Ligand for Dopamine Transporters", Europ. J. of Pharm. 194: 133–134, 1991.
Clarke et al., "Compounds Affecting the Central Nervous System . . . ", J. of Med. Chem. 16:1260–1267, 1973.
Dagani, R., "Cocaine analog for Parkinsonism Studies", C&EN 25–26, Oct. 1991.
Madras et al., "Cocaine Receptors Labeled by . . . ", Mol. Pharm. 36:518–524, 1989.
"Membrane Receptors", Poster 342, The FASEB Journal 4:A325, Feb. 26, 1990.
Milius et al., "Synthesis and Receptor Binding of N–Substituted Tropane Derivatives. High–Affinity Ligands for the Cocaine Receptor", J. of Med. Chem. 34:No. 5, 1991.
Seitz et al., "Tritiodestannylation. Synthesis of a Specifically Labelled . . . ", Synthetic Communications 11:281–286, 1981.

*Primary Examiner*—Gary E. Hollinden
*Assistant Examiner*—Michael G. Hartley
*Attorney, Agent, or Firm*—Weingarten, Schurgin, Gagnebin & Hayes LLP

[57] ABSTRACT

An iodinated neuroprobe is provided for mapping monoamine reuptake sites. The iodinated neuroprobe is of the formula:

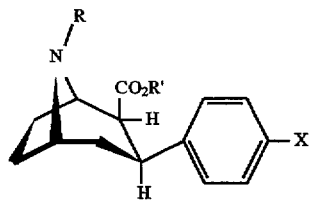

wherein:

R=aryl, substituted aryl, heterocyclic, $CO(CH_2)_nY$, $(CH_2)_n$, $CHF_2$, and $(CF_2)_nY$, wherein:
Y=Cl, Br, I, $(CH_2)_m$, aryl, substituted aryl, heterocyclic $CO_2H$, $CO_2R^3$, $CO_2NR^3R^4$, OH, $OR^3$, $CH(OR^3)_2$, $CR^3(OR^4)_2$, $OCOR^3$, $OSO_2R^3$, $OCONR^3R^4$, $OCOOR^3$, $CONR^3R^4$, $NR^3R^4$, $NR^3COR^4$, $NR^3CO_2R^4$, $NR^3CONR^4R^5$, NCS, NCO;
$R^3$, $R^4$ and $R^5$=alkyl, substituted alkyl, alkenyl, substituted alkenyl, aryl, substituted aryl, or heterocyclic;
m=3–8; and
n=1–6;

R'=$C_wH_{2w+1}$ wherein w=0–6 and C includes an isotope of carbon; and

X=an isotope of Cl, an isotope of Br, an isotope of F, an isotope of I, or $Sn(R''_1 R''_2 R''_3)$, wherein
$R''_1$=a $C_pH_{2p+1}$ group where p=1–6, or an aryl group;
$R''_2$=a $CH_{p+1}$ group where p=1–6, or an aryl group; and
$R''_3$=a $C_pH_{2p+1}$ group where p=1–6, or an aryl group.

Related analogs are also provided. Additionally, a precursor of a radiolabeled neuroprobe and a kit for preparing the iodinated neuroprobe are provided.

11 Claims, 4 Drawing Sheets

REGION INFORMATION

| NAME | ACTIVITY | AREA | MEAN |
|---|---|---|---|
| A) R. STRIATAL | 249688 | 184 | 1357 |
| B) L. STRIATAL | 261096 | 184 | 1419 |
| C) R. CORTICAL | 27156 | 186 | 146 |
| D) L. CORTICAL | 33108 | 186 | 178 |

IODINATED NEUROPROBE FOR MAPPING MONOAMINE REUPTAKE SITES

CROSS REFERENCE TO RELATED APPLICATIONS

This Application is a continuation-in-part application of application Ser. No. 08/185,689, filed Jan. 24, 1994, now U.S. Pat. No. 5,439,666, which is a continuation of application Ser. No. 07/841,617, filed Feb. 25, 1992, now U.S. Pat. No. 5,310,912.

FIELD OF THE INVENTION

This invention relates to neuroprobes for mapping monoamine reuptake sites in the brain, and particularly to a neuroprobe that can also serve as a radiotracer for use in single-photon emission computed tomography (SPECT) and positron emission tomography (PET) for imaging of such reuptake sites.

BACKGROUND OF THE INVENTION

A brain consists of a plurality of neurons that interact by exchanging chemical messengers. Each neuron generates neurochemicals, referred to as neurotransmitters; neurotransmitters act at sites on the cellular membrane of a neuron, the sites being referred to as receptors. Receptors are associated with either ion channels through the cellular membrane or secondary neurochemical messenger systems. By contrast, reuptake sites are molecular complexes which transport chemicals across the cellular membrane of a neuron. When a neurotransmitter has served its function, it is removed from the vicinity of the receptor by being bound to a reuptake site which transports the neurotransmitter to the interior of the neuron.

Just as there are many specialized neurons in the brain, there are also a variety of neurotransmitters, associated receptors, and reuptake sites. The distribution of specialized neurons depends upon the particular organism under study, and the state of health of that organism.

A neuron can be classified according to the type of neurotransmitter that it uses to communicate with other neurons. Certain types of neurons can be found predominantly in particular regions of the brain. For example, the striatal region of a mammalian brain is innervated by neurons using dopamine as a neurotransmitter. The striatum also contains a large number of non-dopaminergic neurons that have dopamine receptors. Certain compounds, such as cocaine, have a preferential affinity for dopamine reuptake sites, and therefore tend to bind to such reuptake sites. The effect of a molecule such as cocaine upon a dopamine reuptake site is to inhibit reuptake of the neurotransmitter dopamine, leaving more dopamine available in the vicinity of the dopamine receptors.

In certain neurological diseases, such as Parkinson's disease, distinct groups of neurons lose their normal physiological functioning. Consequently, the abnormal neurons may behave differently in the presence of some neurotransmitters, and may also produce neurotransmitters in a manner that differs from a healthy neuron.

The major neurotransmitters, dopamine, norepinephrine, and serotonin, are referred to collectively as the monoamine neurotransmitters. Many neurons have receptors adapted to receive at least one of these neurotransmitters. Parkinson's disease is caused by the degeneration of some of the dopaminergic neurons in the brain. The neurons lost in Parkinson's disease have a large number of dopamine reuptake sites; cocaine and chemical analogs of cocaine have an affinity for such reuptake sites.

A radioisotope is commonly incorporated in molecules that have a demonstrated binding affinity for a particular type of neuroreceptor, and such molecules are commonly used as neuroprobes. The localization of neuroprobes can be used to find specialized neurons within particular regions of the brain. It is also known that a neurological disease can be detected by observing abnormal binding distributions of a neuroprobe. Such abnormal binding distributions can be observed by incorporating a radionuclide within each molecule of the neuroprobe with a high binding affinity for the particular reuptake sites of interest. Then, an imaging technique can be used to obtain a representation of the in vivo spatial distribution of the reuptake sites of interest.

In single photon emission computed tomography (SPECT) imaging, the most commonly used radionuclides are heavy metals, such as $^{99m}$Tc. Heavy metals are very difficult to incorporate into the molecular structure of neuroprobes because such probes are relatively small molecules (molecular weight less than 400).

In positron emission tomography (PET), the radiohalide $^{18}$F (fluorine) is commonly used as a substitute for H (hydrogen) in radiopharmaceuticals because it is similar in size. Not all halogens will work, however. For example, I (iodine) is much larger than both H and F, being approximately half the size of a benzene ring. However, due to the small size of typical radiopharmaceuticals for use as neuroprobes, the presence of iodine markedly changes the size of the compound, thereby altering or destroying its biological activity.

In addition, the presence of iodine in a neuroprobe tends to increase its lipophilicity, and therefore increases the tendency of the neuroprobe to engage in non-specific binding. For example, paroxetine is a drug with high affinity and selectivity for serotonin reuptake sites, and [$^3$H]paroxetine has been shown in rodents to be a useful in vivo label (Scheffel, U. and Hartig, P. R. J. Neurochem., 52: 1605–1612, 1989). However, several iodinated analogs of this compound with iodine attached at several different positions had unacceptably low affinity, in fact being one tenth of the affinity of the parent compound. Furthermore, when the iodinated compound was used as an in vivo radiolabeled neuroprobe, non-specific binding activity was found to be so high that no measurable portion of the brain uptake appeared to be specifically bound to the serotonin reuptake site. Thus, the iodinated form of paroxetine is not useful as an in vivo probe.

The addition of iodine to a neuroprobe can unfavorably alter its biological properties. For example, tomoxetine has high affinity and selectivity for norepinephrine reuptake sites. However, when tomoxetine is iodinated, e.g. to form R-4-iodotomoxetine, the resulting labeled compound has low affinity for such reuptake sites, and relatively high affinity for serotonin reuptake sites. In vivo labeling studies have shown that it is an unacceptably poor probe even for the serotonin reuptake sites because it exhibits low total brain uptake and immeasurably low specific uptake.

An iodinated compound can be useful as an in vitro probe, but may be useless as an in vivo probe, because an in vivo probe must meet the requirements associated with intravenous administration of the probe to a living subject. Reasons for the loss of in vivo utility include the fact that the compound may be metabolized too quickly, that it may not cross the blood-brain-barrier, and that it may have high non-specific uptake into the lipid stores of the brain. In vitro homogenate binding studies remove these obstacles by isolating the brain tissue from hepatic metabolic enzymes, by homogenizing the brain tissue so as to destroy the blood-brain-barrier, and by diluting the brain tissue so as to decrease the concentration of lipids in the assay tube. Accordingly, it cannot be assumed that a probe will be useful in both in vivo and in vitro modalities.

An in vivo SPECT probe was developed by iodinating cocaine. However, this probe shows a binding affinity and specificity no better than cocaine itself, which is inadequate for purposes of SPECT imaging.

SUMMARY OF THE INVENTION

An iodinated neuroprobe is provided for mapping monoamine reuptake sites. The iodinated neuroprobe is of the formula:

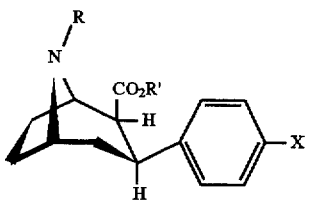

wherein R can be aryl, substituted aryl, heterocyclic, $CO(CF_2)_nY$, $(CF_2)CHF_2$, and $(CH_2)_nY$. Y can be Cl, Br, I, $(CH_2)_m$, aryl, substituted aryl heterocyclic, $CH_2H$, $CO_R^3$, $CO_2NR^3R^4$, OH, $OR^3$, $CH(OR^3)_2$, $CR^3(OR^4)_2$, $OCOR^3$, $OSO_2R^3$, $OCONR^3R^4$, $OCOOR^3$, $CONR^3R^4$, $NR^3R^4$, $NR^3COR^4$, $NR^3CO_2R^4$, $NR^3CONR^4R^5$, NCS, NCO. $R^3$, $R^4$ and $R^5$ can be alkyl, substituted alkyl, alkenyl, substituted alkenyl, aryl, substituted aryl, or heterocyclic; m=3–8 and n=1–6. R' can be $C_wH_{2w+1}$ wherein w=0–6 and C includes an isotope of carbon, including at least one radioactive isotope of carbon. X can be an isotope of Cl, an isotope of Br, an isotope of F, an isotope of I, or $Sn(R''_1 R''_2 R''_3)$ wherein $R''_1$, $R''_2$, and $R''_3$ are $C_pH_{2p+1}$ groups where p=1–6, or an aryl group.

For each of the foregoing embodiments there is provided a precursor of the radiolabeled neuroprobe that lacks a radiotracer atom, and a kit for preparing an associated iodinated neuroprobe. Also included are derivatives of the neuroprobes that include $^{18}F$ substituted onto R. As used herein "β-CIT" and "CIT" refer to N-(N', N'-dimethyl) acetamido-2β-carbomethoxy-3β-(4-iodophenyl) nortropane. As used herein, the substituent $(CH_2)_m$ refers to a cycloalkyl group, e.g., cyclopropyl, cyclobutyl, cyclopentyl, cyclohexyl, and the like.

Both the radiostable and radioactive variants of the iodinated neuroprobe of the invention are useful for human and non-human research. For example, in vivo and in vitro experiments can be performed using the compounds of the invention to study dopamine reuptake sites generally, and cocaine binding sites in particular.

DESCRIPTION OF THE DRAWING

The invention will be more fully understood from the following detailed description, in conjunction with the accompanying figures in which.

DETAILED DESCRIPTION OF THE INVENTION

Figure 1:
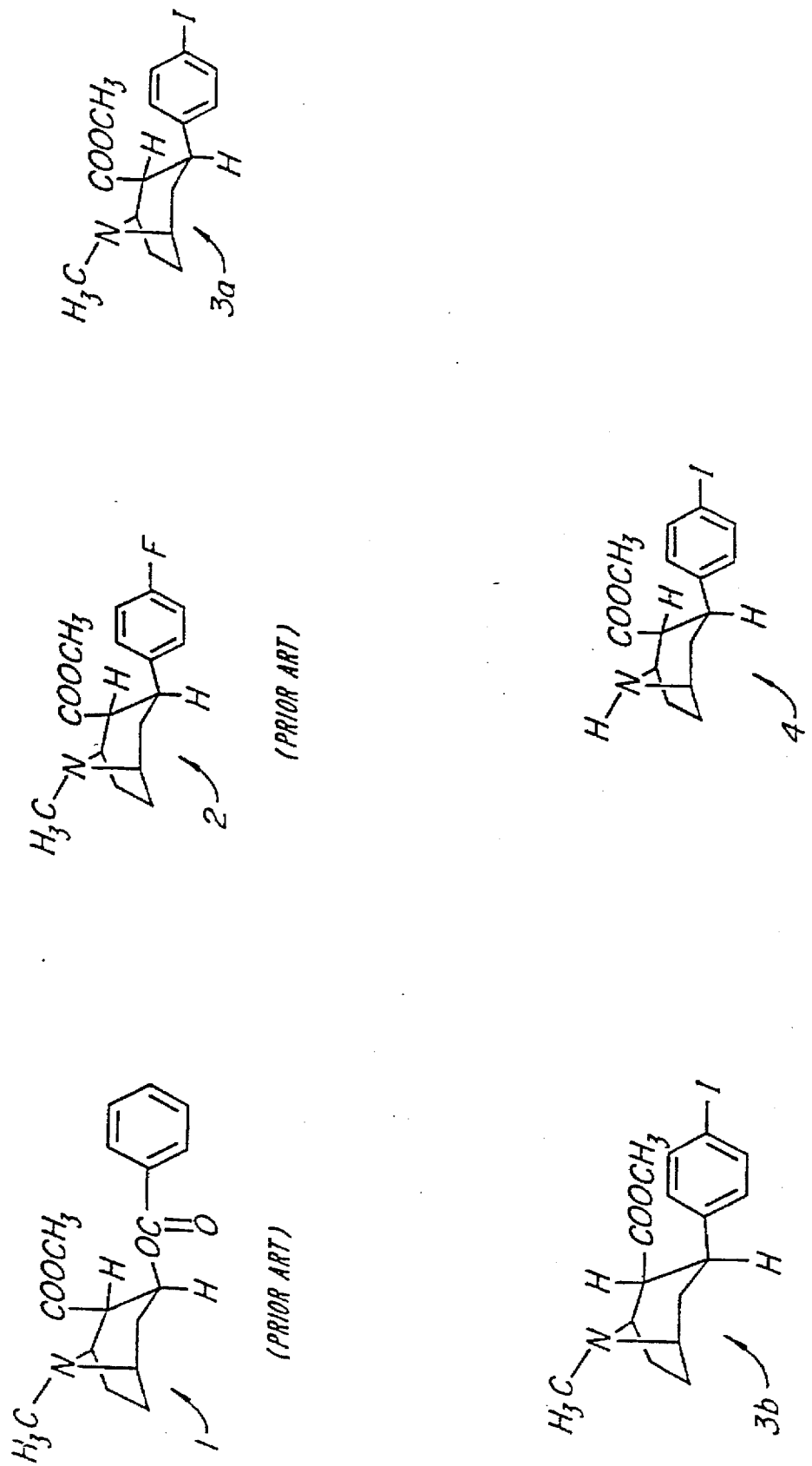
FIG. 1 shows prior art compounds compared to compounds of the invention.

Metabolically stable cocaine analogs such as 2β-carbomethoxy-3β-(4-iodophenyl)-tropane), an iodine-containing analog of β-CIT (also designated RTI-55), as shown in FIG. 1, compound 3, have high affinities for dopamine and serotonin reuptake sites in brain. As will be discussed below, [$^{123}I$]-β-CIT is shown to be a SPECT (single photon emission computed tomography) radiotracer for dopamine and serotonin reuptake sites.

[$^{123}I$]-β-CIT was prepared by reaction of the corresponding tributyltin precursor with no-carrier added Na[$^{123}I$] in the presence of peracetic acid, followed by preparative HPLC on a C-18 column with methanol/water/triethylamine (75/25/0.2) at a flow rate of 1.0 ml/min. The final product was formulated in 6 ml sterile saline containing 5-10% ethanol.

Six SPECT experiments were performed in four female baboons (10 kg Papio anubis) under isoflurane anesthesia. The animals were injected with 10.6±1.4 mCi[$^{123}I$]-β-CIT and scanned for 333±25 min in either the 810X Brain Imager (Strichman Medical Equipment; five experiments) or the ASPECT device (Digital Sintigraphics, Cambridge, Mass.; one experiment), with these and subsequent data expressed as means ±S.E.M. Serial 2-6 min images were reconstructed assuming uniform attenuation equal to that of water in an ellipse drawn around the brain. Data were decay-corrected to the time of injection.

Figures 2, 4:
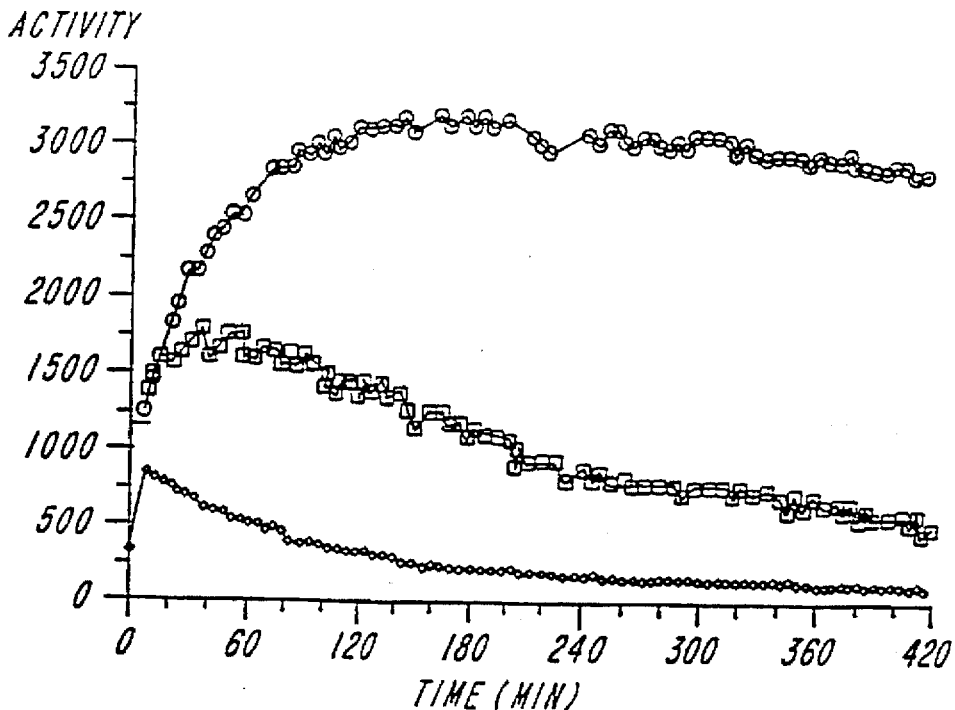
FIG. 2 shows regional activity in a baboon brain following injection of a compound of the invention.
FIG. 4 shows regional areas of brain uptake of a compound of the invention.

FIG. 2 illustrates regional activity in baboon brain following injection of 9.6 mCi [$^{123}I$]CIT. Activity is expressed in arbitrary units known from phantom studies to be linear with radioactive concentrations. The activities in three brain regions are graphed wherein the trace of open circles is the striatum, the trace of open squares is the midbrain, and the trace of open diamonds is the cerebellum. The highest activities were found in the striatal region and reached peak levels at 179±9 min (n=6) post injection (p.i.)(FIG. 2). Striatal activity was monitored in two animals for an additional 190 and 260 min post peak values. In one animal, striatal activity was virtually unchanged for the remaining 190 min of the experiment. With reference to FIG. 2, in the second animal, washout of striatal activity was fit to an exponential function and had $t_{1/2}$=27 h (r=0.92).

The brain region which approximately overlay the mesencephalon or midbrain area had the second highest levels of activity. Midbrain values peaked earlier (45±16 min p.i.; n=6) and washed out more rapidly ($t_{1/2}$=294±59 min; r=0.98±0.01; n=3) than that in the striatum.

At the time of peak striatal uptake, the ratios of regional brain activities were: striatum (100%); hypothalamus (38.1±5.2%); occipital lobe (13.5±0.8%); temporo-parietal lobes (14.3±2.0%); frontal lobe (10.3±1.0%); and cerebellum (10.0±1.5%), all measured with n=6.

(−)Cocaine (FIG. 1, compound 1) and CFT (FIG. 1, compound 2), both potent dopamine and serotonin reuptake inhibitors, induced rapid and dose-dependant displacement of both striatal and midbrain activity. (−)Cocaine (2.9 μmol/kg) administered at 200 min p.i. caused displacement of 17% of striatal and 49% of midbrain levels within 30–65 min. At 14.7 Fmol/kg administered at 230 min p.i., the corresponding cumulative displacements were 62% and 77%, respectively, within the same period of time.

CFT (0.4 μmol/kg) administered i.v. at 180 min p.i. caused displacement of 57% of striatal and 72% of midbrain levels within 60–120 min. At 2.0 μmol/kg administered at 298 min p.i., the corresponding cumulative displacements were 83% and 91%, respectively, within the same period of time.

In contrast, citalopram (a selective serotonin reuptake inhibitor) caused greater displacement of midbrain than striatal activity. At a dose of 8.3 μmol/kg i.v. at 190 min p.i., midbrain levels decreased by 57% during the following 110 min, compared to only 5% decrease in striatal activity during the same period.

[$^{123}$I]-β-CIT appears to be a useful SPECT tracer of the dopamine and serotonin reuptake sites. Brain uptake and washout are relatively slow in comparison to cocaine itself and are consistent with the metabolically resistant chemical structure of β-CIT and the location of the radioiodine in a chemically stable position. Striatal uptake appears to largely represent labeling of the dopamine reuptake site, whereas that in the midbrain is largely associated with the serotonin reuptake site. The high ratios of striatal to cerebellar activity of [$^{123}$I]-β-CIT are consistent with low non-specific uptake of the tracer, and suggest that [$^{123}$I]-β-CIT may be a useful clinical marker of dopaminergic deficiencies in Parkinson's disease.

Referring again to FIG. 1, in a second study (Neumeyer, J. L. et al., J. Med. Chem., 34: 3144–3146 (1991)), the potent cocaine analog 2β-carbomethoxy-3β-(4-fluorophenyl) tropane (compound 2) (also referred to as CFT or WIN 35,428 (Clarke, R. L., et al., 1973; Madras, B. K. et al., 1989)) when tritiated or labeled with $^{11}$CH$_3$ was found to be superior to [$^3$H]cocaine or [$^{11}$C]cocaine (Fowler, J. S. et al., Synapse 4: 371–377 (1989)) as a radioligand probe for cocaine receptors in terms of higher affinity and larger residence time on the dopamine reuptake site. For further development of analogues suitable for PET and SPECT imaging, 2β-carbomethoxy-3β-(4-iodophenyl) tropane were synthesized and characterized (compound 3a; designated as β-CIT in analogy to CFT, its corresponding, N-demethylated derivative (compound 4; designated as nor-CIT), and the C$_{2\alpha}$ isomer (compound 3b), as shown in FIG. 1.

Figure 3:
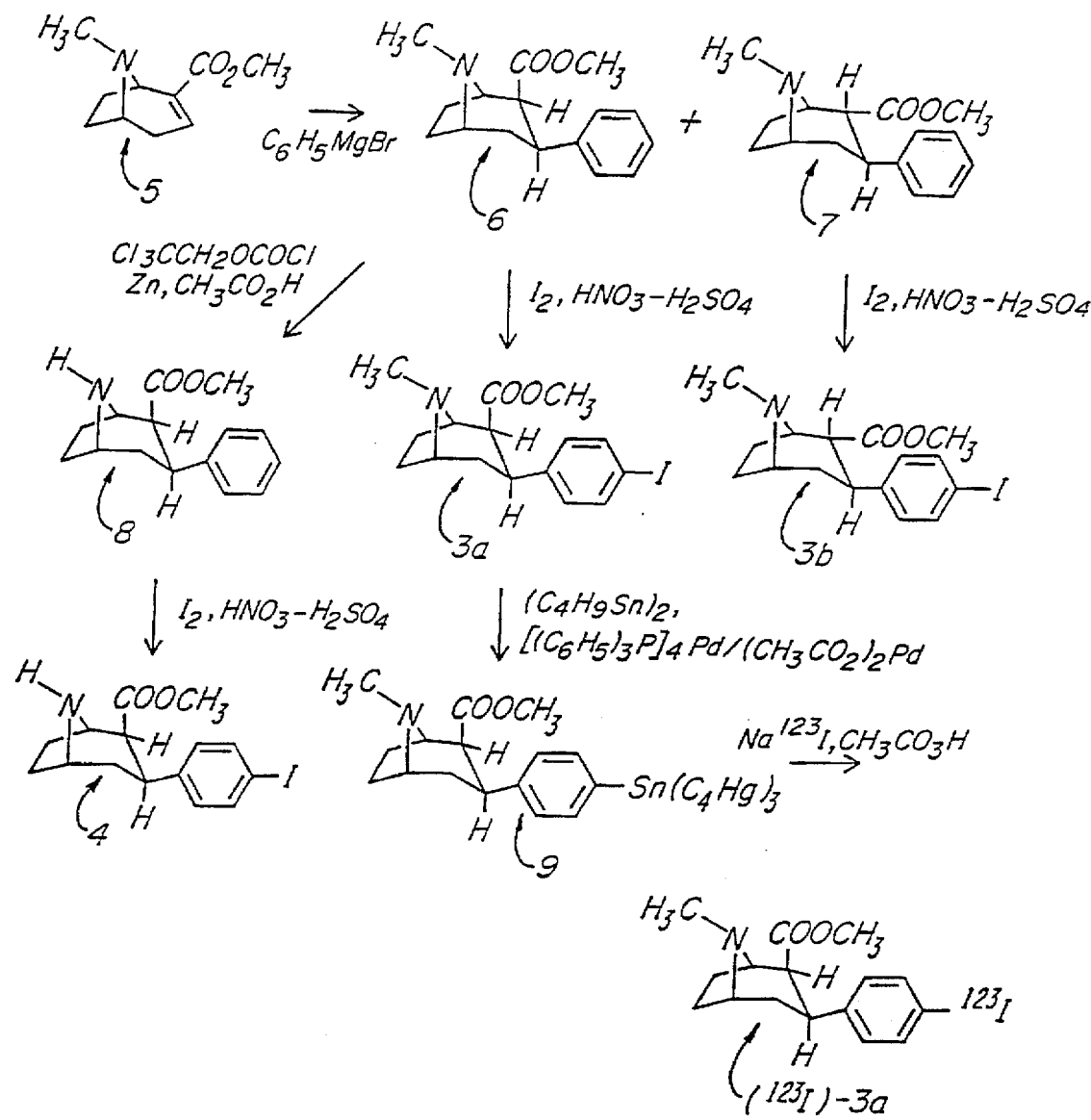
FIG. 3 shows a synthesis route for a compound of the invention.

Referring to FIG. 3, a synthesis protocol for [$^{123}$I]-β-CIT is described. Ecgonidine methyl ester (compound 5) was prepared from cocaine by the procedure of Clarke et al. (1973). Treatment of compound 5 with phenylmagnesium bromide and subsequent workup with trifluoroacetic acid at low temperature gave a mixture of C$_2$ epimers (compound 6) (45%) and (compound 7) (31%), which were separated by flash chromatography (silica; CH$_2$Cl$_2$/CH$_3$OH, 25:1). Direct iodination of compound 6 with I$_2$/HNO$_3$/H$_2$SO$_4$ gave the para-substituted compound 3a (β-CIT) as an oil; 62%; [α]$_{25}$D −2.0° (c=0.85, CHCl$_3$). D-Tartrate salt; mp 72°–74° C.; [α]$^{25}$D −87.7° (c=1.5, CH$_3$OH). Iodination of compound 7 by the same procedure gave compound 3b (α-CIT) as an oil; 39% [α]$^{25}$D +44° (c=2.5, CHCl$_3$). 1,5-naphthalenedisulfonate salt; mp 139°–140 ° C. N-Demethylation of compound 6 was accomplished by conversion to its 2,2,2,-trichloroethyl carbamate followed by reduction (Zn/acetic acid) to yield compound 8 by the procedure previously described by Milius, R. A., et al., J. Med. Chem. 34 1728–1731 (1991), herein incorporated by reference, followed by iodination to yield nor-CIT (compound 4), which was isolated as a yellow crystalline solid (free base 48% from compound 6): mp 149°–151° C.; [α]$^{25}$D −67.4° (c=1, CHCl$_3$).

[$^{123}$I]-β-CIT (compound $^{123}$I-3a) was synthesized from nonradioactive β-CIT (compound 3a) by conversion to the corresponding tributyltin derivative (compound 9). Treatment of compound 3a with bis(tributyltin), tetrakis (triphenylphosphate)palladium(0), and palladium (II) acetate in refluxing tetrahydrofuran gave compound 9 as a colorless waxy solid after flash chromatography (silica, stepwise gradient, hexane to hexane/ether, 75:25) in 26% yield from 3a. The 300 MHz NMR (CDCl$_3$) of compound 9 was consistent with the assigned structure. Reaction of compound 9 with carrier-free Na$^{123}$I in the presence of peracetic acid gave compound [$^{123}$I]-3a. The radioiodinated product compound [$^{123}$I]-3a was purified by preparative HPLC (Novapak C$_{18}$, MeOH/H$_2$O/Et$_3$N, 75:25:0.2, 1.0 mL/min; t$_R$ 6.7 min) and formulated in normal saline containing 5% ethanol an 1% ascorbic acid. Compound [$^{123}$I] -3a was obtained in average overall yield of 60.0±13.4% and with radiochemical purity of 97.6±1.6%. The tributyltin precursor used in radiolabeling contained about 7 mol % CIT carrier, resulting in an $^{123}$I product having a specific activity of about 2000 ci/mmol.

The affinities of cocaine (compound 1), α-CIT (compound 3b), β-CIT (compound 3a), and β-CFT (compound 2) for the dopamine and serotonin reuptake sites were determined from radioligand displacement studies using tissue homogenates prepared from baboon and rat brain, shown in Table 1 below.

TABLE I

In Vitro Radioligand Binding Data for Cocaine and 3-(4-Halophenyl) Analogues*

| analogue | displacement of [$^3$H]CFT | | displacement of [$^3$H]paroxetine | |
|---|---|---|---|---|
| | IC$_{50}$ (nM) | Hill slope (nH) | IC$_{50}$ (nM) | Hill slope (nH) |
| 1(cocaine) | 221 ± 14 | 0.69 ± 0.06 (3) | 207 ± 66 | 0.73 ± 0.12 (5) |
| 2(β-CFT) | 15.3 ± 1.2 | 0.75 ± 0.01 (3) | 479 ± 59 | 1.34 ± 0.22 (3) |
| 3b(α-CIT) | 87.6 ± 2.9 | 0.70 ± 0.07 (2) | 210 ± 86 | 0.73 ± 0.04 (2) |
| 3a(β-CIT) | 1.6 ± 0.15 | 0.79 ± 0.04 (3) | 3.78 ± 0.53 | 0.82 ± 0.08 (6) |

The data in Table 1 represent radioligand binding of [$^3$H]CFT (0.5 nM) to dopamine reuptake sites in tissue homogenates prepared from primate striatum and binding of [$^3$H]paroxetine to serotonin reuptake sites in homogenates prepared from rat cortical membranes. The IC$_{50}$ value is the concentration of displacing analogue required to decrease specific radioligand binding by 50%. Values represent means ±SEM (of n experiments).

With reference to FIG. 4, five SPECT (single photon emission computer tomography) experiments were performed with four female baboons (*Papio anubis*, 10–12 kg) under isoflurane anesthesia. Animals were injected i.v. with 8.1±1.4 mCi [$^{123}$I]-β-CIT (with these and subsequent data expressed as mean ±SEM) and scanned for 300±41 min with the 810X Brain Imager (Strichman Medical Equipment, Medfield, Mass.). Serial 1–2 min images were reconstructed assuming uniform attenuation equal to that of water in an ellipse drawn around the brain. Data were decay corrected to time of injection.

Figure 5A:
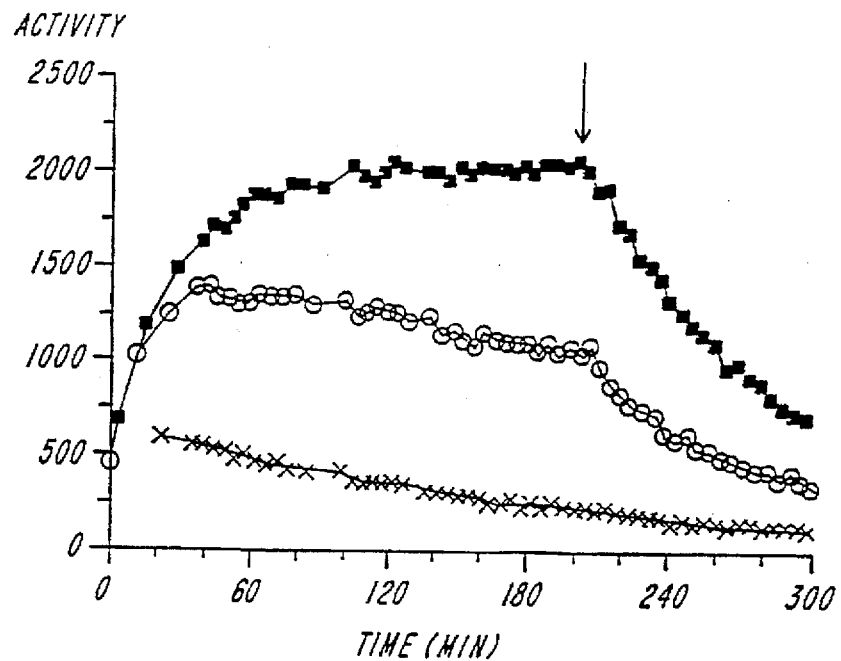
FIG. 5A shows regional activity in a baboon brain following injection of compound of the invention.
Figure 5B:
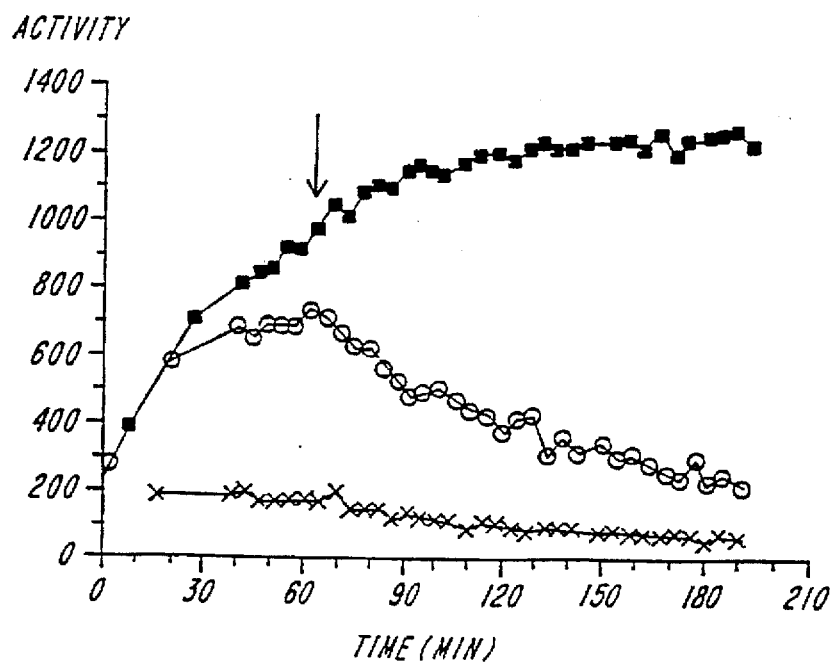
FIG. 5B shows regional activity in a baboon brain following injection of a compound of the invention.

FIGS. 5A and 5B illustrate regional activity in baboon brain following iv injection of 12.1 mCi (FIG. 5A) and 4.2 mCi (FIG. 5B) [$^{123}$I]CIT. Activity is expressed in arbitrary units known from phantom studies to be linear with radioactive concentrations. Displacing agents (FIG. 5A: 13 μmol Lu-19-005 per kg; FIG. 5B: 7.4 μmol Citalopram per kg) were injected iv at the times marked with arrows. Activities in three brain regions are graphed wherein the trace of filled squares is the striatum, the trace of open circles is the midbrain, and the trace of Xs is the cerebellum. Highest brain uptake overlay the striatal region and peaked at 154±19 min postinjection (pi) of the radioligand and showed striatal to cerebellar ratios at that time of 9.8±1.6. Washout of striatal activity was followed for an additional 200 and 260 min in two of three control animals and showed 0% and 12% decreases, respectively, from time of striatal peak to end of the experiment.

With reference to FIGS. 5A and 5B, the brain area with second highest activities approximately overlays the midbrain and showed peak levels at 43±5 min pi (n=5) and had a faster washout than striatal activity.

The pharmacological specificity of the in vivo labeling of [$^{125}$I]-β-CIT was examined with displacement of brain activity by indatraline (also designated Lu 19-005), a potent agent for the dopamine and serotonin reuptake sites, and citalopram, an agent selective for the serotonin reuptake site. Indatraline (3 μmol/kg iv) injected at 200 min pi radioligand caused significant decrease of both striatal and midbrain activity, as shown in FIG. 5A. During the 100 min period after injection of Lu 19-005, striatal activity decreased by 65% compared to a mean decrease of 2% during the same period in the two control animals followed for that length of time. In contrast, citalopram (7.4 μmol/kg iv) injected 60 min pi radioligand showed a selective decrease of midbrain activity, as shown in FIG. 5B. Citalopram caused a 48% decrease of midbrain activity during the 60-min period after injection, in comparison to 16±3% decrease (n=3) of midbrain activity in control animals followed during this same period.

These results showed that [$^{123}$I]-β-CIT was a useful SPECT probe of monoamine reuptake sites in primates. The majority of striatal activity was associated with dopamine reuptake sites, and the majority of midbrain activity was associated with serotonin reuptake sites, which is consistent with the densities of these monoamine transporters measured in postmortem primate brains. Brain washout of activity was relatively slow, in part because of the high affinities of β-CIT for the monoamine transporters. In addition, the iodine atom appears to be in a relatively metabolically resistant position, since whole body scanning showed low thyroid uptake, which is indicative of a slow in vivo rate of deiodination. [$^{123}$I]-β-CIT and [$^{11}$C]-β-CIT may be useful clinical markers of dopaminergic and serotonergic innervation in human disorders such as Parkinson's disease and depression, which are thought to have abnormalities in these neuro-transmitter systems.

EXAMPLES OF SYNTHESES

Example 1

2-beta-Carbomethoxy-3-beta-(4-iodophenyl)tropane

A mixture of 2-beta-carbomethoxy-3-beta-phenyltropane (See Example 1A below and Milius et al. J. Med. Chem., 1991, 34, 1728) (2.9 g, 11.5 mmol) and I$_2$ (3 g. 11.8 mmol) in 25 ml of glacial acetic acid was stirred and treated dropwise with a mixture of 4.7 mL of concentrated nitric acid and 4.7 mL of concentrated sulfuric acid. The reaction mixture was heated to 55° C. and stirred for 2 hours, then cooled to room temperature and poured onto ice (100 g) and filtered. The pH of the filtrate was adjusted to 9.5 by the addition of concentrated ammonium hydroxide at 0°–5° C. The resulting precipitate was removed by filtration and dissolved in methylene chloride (250 ml). The filtrate was extracted with two 50 mL portions of methylene chloride. The extracts and solution of precipitate were combined, washed with brine (50 ml) and dried over magnesium sulfate. After the removal of the solvent, 3.9 g (90.4%) of 2-beta-carbomethoxy-3-beta-4-iodophenyltropane free base was obtained as an oil.

The free base was dissolved in methanol (20 ml) and combined with 1.5 g of D-(−)tartaric acid in 20 ml of methanol. After the removal of methanol under reduced pressure, the residue was recrystallized from methanol ether (3:1) to give 2-beta-carbomethoxy-3-beta-(4-iodophenyl) tropane D-tartrate salt as white crystals, m.p. 72°–74° C. $C_{16}H_{20}NO_2I \cdot C_4H_6O_6$. Calculated: C: 44.88, H: 4.89, N: 2.62. Found: C: 44.70, H: 4.94, N: 2.57. [alpha]$_D^{22}$=−87.7° (c=0.3, CH$_3$OH).

Example 1A 2-beta-Carbomethoxy-3-beta-phenyltropane

A 2M ethereal solution of phenylmagnesium bromide (83 mL, 166 mmol) in a 500-mL 3-neck round-bottom flask equipped with mechanical stirrer, addition funnel, and nitrogen inlet tube was diluted with 83 mL of anhydrous diethyl ether and cooled to −20° C. under an atmosphere of dry nitrogen. A solution of anhydroecgonine methyl ester, prepared from cocaine (1) (15 g, 82.8 mmol) in anhydrous ether (75 mL) was added dropwise. The heterogeneous mixture was stirred for 1 h at −20° C., then poured into an equal volume of ice and water, and acidified by the dropwise addition of 2M HCl. The aqueous layer was made basic by the addition of concentrated ammonium hydroxide, saturated with NaCl, and extracted with diethyl ether. The combined extracts were dried (Na$_2$SO$_4$) and concentrated in vacuo to give a brown oil. Bulb to bulb distillation (70° C., 0.9 Torr) of the crude product gave a pale yellow oil (16 g, 70%). TLC analysis of the oil (silica, pentane/diethyl ether/ 2-propylamine, 15:5:0.8) showed it to be a mixture of the C-2 alpha and beta epimers. The beta isomer was isolated by silica gel chromatography (pentane: diethyl ether: isopropyl amine, 70:30:3). m.p. 63°–66° C. (lit: 62°–64,5° C.: Clarke et al. J. Med. Chem. 16: 1260 (1973)).

Example 2

2-alpha-Carbomethoxy-3-beta-iodophenyltropane

The mixture of alpha and beta-2-carbomethoxy-3-beta-iodophenyltropanes prepared as described in Example 1 were separated by silica gel chromatography as described in Example 1. Fractions containing the alpha-2-carbomethoxy-3-beta-iodophenyltropane were pooled and concentrated in vacuo. The free base thus obtained was treated with naphthalene-1,5-disulfonic acid. The crude salt was recrystallized from acetonitrile to give the 2-alpha-carbomethoxy-3-beta-iodophenyltropane naphthalene-1,5-disulfonate salt, m.p. 166°–168° C. $C_{16}H_{20}NO_2I \cdot C_{10}H_6(SO_3H)_2 \cdot 2H_2O$. Calculated: C: 40.01, H: 4:55, N: 1.97, I: 17.90; Found: C: 43.94, H: 4.55, N: 1.91, I: 17.99.

Example 3

2-beta-Carbomethoxy-3-beta-(4-iodophenyl)nortropane

A solution of 2-beta-carbomethoxy-3-beta-(4-iodophenyl) tropane (410 mg, 1.5 mmol) in toluene (20 mL) was treated with of 2,2,2-trichloroethyl chloroformate (1 mL, 7.3 mmol). The mixture was heated at 120° C. for 1 hour, cooled to room temperature, and evaporated to dryness in vacuo. The residue was partitioned between methylene chloride and water. The organic layer was separated, dried ($N_2SO_4$), and concentrated in vacuo to give the trichloroethyl chloroformate as a dry foam. The crude carbamate was dissolved in 50% aqueous acetic acid, treated with 200 mg (0.0067 g-atom) of zinc dust, and stirred at room temperature for 16 hours. The reaction mixture was filtered adjusted to pH 7 with concentrated ammonium hydroxide, saturated with NaCl, and extracted with diethyl ether. The extracts were combined, dried ($Na_2SO_4$), and concentrated in vacuo. The residue was purified by flash chromatography (silica, pentane/diethyl ether/isopropylamine, 3:7:0.7) to afford 2-beta-carbomethoxy-3-beta-(4 -iodophenyl)nortropane, which was isolated as a yellow crystalline solid, m.p 149°–151° C.; [alpha]$^{25}_D$ –67 4° (c=1, $CHCl_3$).

Example 4

2-beta-Carbomethoxy-3-beta-(4-iodophenyl)-8-(3-fluoropropyl)-nortropane

A solution of 2-beta-carbomethoxy-3-beta-(4-iodophenyl)-nortropane (371 mg, 1.0 mmol), 1-bromo-3-fluoropropane (155 mg, 1.1 mmol), and triethylamine (0.5 mL) in dry toluene (20 mL) was stirred under an atmosphere of dry nitrogen and heated to reflux. After four hours, the reaction mixture was cooled to room temperature and filtered. The filtrate was concentrated under reduced pressure, and the residue chromatographed on a silica column (eluant: diethyl ether). Concentration of product-containing fractions gave 2-beta-carbomethoxy-3-beta-(4-iodophenyl)-8-(3-fluoropropyl)nortropane as a white solid, m.p. 78.5°–79.5° C. $C_{18}H_{23}NO_2FI$, Calculated: C: 50.13, H: 5.34, N: 3.25; Found: C: 50.27, H: 5.26, N: 3.15.

Example 5

2-beta-Carbomethoxy-3-beta-(3-fluoro-4-iodophenyl)tropane

A mixture of 2-beta-carbomethoxy-3-beta-(3-fluorophenyl) tropane (400 mg, 1.44 mmol), silver sulfate (400 mg, 1.3 mmol), iodine (600 mg, 2.36 mmol) and 80% sulfuric acid (9 Ml) was stirred for five days at room temperature. The reaction mixture was poured into 150 mL of ice and water, made basic by the addition of concentrated ammonium hydroxide, and extracted with three 60 mL portions of chloroform. The combined extracts were washed sequentially with solutions of 10% sodium bisulfite, 5% sodium carbonate and water, then dried over sodium sulfate, and filtered. The filtrate was concentrated in vacuo and the oily residue was redissolved in chloroform and treated with a solution of p-toluene sulfonyl chloride in chloroform. The resulting solid was repeatedly recrystallized from water and ethanol to give 2-beta-carbomethoxy-3-beta-(3-fluoro-4-iodophenyl)tropanetosylate salt as a white crystalline solid, m.p. 68°–70° C. (soften, 45° C.), $C_{16}H_{19}FINO_2 \cdot C_7H_8SO_3 \cdot H_2O$: Calculated: C: 46.55,H: 4.93, N: 2.36; Found: C: 46.34, H: 4.86, N:1.99.

Example 6

2-beta-Carboxy-3-beta-(4-iodophenyl)tropane

A suspension of 2-beta-carbomethoxy-3-beta-(4-iodophenyl)tropane (100 mg, 0.26 mmol) in 2 mL of $H_2O$ was heated at reflux for 10 hours. The resulting solution was cooled to room temperature, and the resulting precipitate was collected by filtration and dried under vacuum overnight to give 70 mg (70%) of 2-beta-carboxy-3-beta-(4-iodophenyl)tropane m.p. 299°–300° C. $C_{15}H_{18}NO_2I.0.5 H_2O$: Calculated C: 47.51, H:5.05, N: 3.69: Found: C: 47.28, H: 4.84, N: 3.69.

Example 7

2-beta-Carbomethoxy-3-beta-benzyloxytropane

A stirred suspension of benzyl bromide (3.0 g, 0.015 mol) and potassium iodide (3.0 g, 0.021 mol) in acetone (20mL) was treated dropwise with a solution of ecgonine methyl ester (2.6 g, 0.014 mol) in acetone (10 mL) at room temperature. The mixture was stirred at room temperature for 70 hours, then heated to reflux and stirred for an additional 8 hours. The reaction mixture was cooled to room temperature and filtered. The filtrate was concentrated in vacuo, the residue dissolved in chloroform (200 mL) and extracted with four 50 mL portions of 2N hydrochloric acid. The combined extracts were made basic by the addition of concentrated ammonium hydroxide. The resulting mixture was extracted with four 20 mL portions of chloroform. The extracts were dried over sodium sulfate and concentrated in vacuo to give 1.7 g of 2-beta-carbomethoxy-3-beta-benzyloxytropane as an oil.

The product was dissolved in acetonitrile (20 mL) and treated with a solution of naphthalene-1,5-disulfonic acid (2.2 g) in acetonitrile (20 mL). The solution was concentrated in vacuo to a syrup, which was diluted with diethyl ether. The resulting precipitate was collected by filtration and dried to give 1.6 g of 2-beta-carbomethoxy-3-beta-benzyloxytropane naphthalene-1,5-disulfonate salt, m.p. 126°–130° C., $C_{17}H_{23}NO_3 \cdot C_{10}H_6(SO_3H)_2 \cdot 2.5\ H_2O$. Elemental analysis: Calculated, C: 52.08, H: 5.83, N: 2.25. Found, C: 52.02, H: 5.69, N: 2.72. [alpha]$_D^{24}$=–25.4° (c=1, $CH_3OH$).

Example 8

2-beta-Carbomethoxy-3-beta-(4-tributylstannylphenyl)tropane

A mixture of 2-beta-carbomethoxy-3-beta-(4-iodophenyl) tropane (250 mg, 0.65 mmol), bis (tributyl) distannane (522 mg, 0.9 mmol), tetrakis (triphenylphosphine)palladium(0) (3 mg) and anhydrous toluene (10 mL) was heated to reflux under an atmosphere of dry nitrogen and stirred for 28 hours. The mixture was filtered, and the filtrate concentrated in vacuo. The residue was applied to a silica gel column and eluted with a mixture of hexane:diethyl ether:isopropyl amine (70:30:3). The fractions containing product were pooled, concentrated in vacuo and treated with pentane to precipitate 2-beta-carbomethoxy-3-beta-(4-tributylstannylphenyl)tropane as a solid. The 300 MHz NMR spectrum was consistent with the assigned structure. [alpha]$_D^{22}$=–8.9° (c=0.4, $CHCl_3$).

Example 9

[$^{123}$I]-2-beta-Carbomethoxy-3-beta-(4-iodophenyl)tropane

To a vial containing 50 µg (0.094 µmol) of 2-beta-carbomethoxy-3-beta-(4-tributylstannylphenyl)tropane was added 50 µL ethanol, 150 µL 0.5M $H_3PO_4$, 125–500 µL (20–30 mCi) [$^{123}$I]NaI solution, and 100 µL (4.2 µmol) 0.042M peracetic acid. After 20–30 minutes, 50 µL of 100mg/mL aqueous $NaHSO_3$ solution was added. Saturated $NaHCO_3$ solution was added, and the mixture extracted with ethyl acetate. The combined extracts were dried ($Na_2SO_4$) and concentrated to dryness. The residue was redissolved in methanol and purified by HPLC (C-18 column, eluant:$CH_3OH:H_2O$:triethylamine; 75:25:0.2). The fraction eluting at the retention time of 2-beta-carbomethoxy-3-beta-(4-iodophenyl)tropane was collected evaporated to dryness and reconstituted in 5% ethanol and 0.1 nM ascorbic acid.

In SPECT applications, the radiostable iodinated neuroprobe of the invention is useful as a reference standard, and can also be used as a dilutant for the radioactive form of the neuroprobe. The radioiodinated compound is generally identified by its chromatographic mobility as compared with a fully characterized reference standard. Thus, preparation of the radioiodinated compound requires the non-radioactive iodinated compound.

To avoid the necessity of storing a radioactive neuroprobe, it is useful to provide a kit containing the non-radioactive iodinated compound and an appropriate oxidizing agent, such as perchloric acid, performic acid, peracetic acid, hydrogen peroxide, hydrogen peroxide with lactoperoxidase, 1,3,4,6-tetrachloro-3α,6α-diphenylglycouril, or a N-chloro-4-methylbenzenesulfonamide sodium salt. Then, the non-radioactive precursor compound can be oxidized in the presence of a suitable radioactive compound, such as the carrier free $Na[^{123}I]$ shown in the synthesis route described herein, any other radioisotope source, such as any solution of a salt of a radioactive isotope of iodine, a reagent containing $^mC_nH_{2n+1}X$, where n=0–6 and X is a leaving group, or a reagent containing $^{18}F$ of the formula $FC_nH_{2n}X$, where n=0–6 and X is a leaving group, to prepare the iodinated neuroprobe at its time and place of use.

Radiolabeled neuroprobes of the invention are also useful in other imaging procedures. For example, an $^{125}I$-labeled neuroprobe can be used in autoradiography or therapy, and an $^{131}I$-labeled neuroprobe is useful as a multiple photon emitter for use in animal studies. Also, $^{11}C$-, $^{14}C$-, and $^{18}F$-labeled neuroprobes can be used in PET imaging.

Both the radiostable and radioactive variants of the iodinated neuroprobe of the invention are useful for human and non-human research. For example, in vivo and in vitro experiments can be performed using the compounds of the invention to study the dopamine transporter generally, and cocaine binding sites in particular.

Additionally, the radiostable version of the neuroprobe of the invention can be used as a drug for influencing dopamine reuptake.

In an alternative embodiment, an intermediate is provided that includes functional moieties attached to N-8. Such moieties include aryl, substituted aryl, heterocyclic, $CO(CH_2)_nY$, $(CF_2)_nCHF_2$, and $(CF_2)_nY$, wherein Y=Cl, Br, I, $(CH_2)_m$, aryl, substituted aryl, heterocyclic, $CO_2H$, $CO_2R^3$, $CO_2NR_3R^4$, OH, $CH(OR^3)_2$, $CR^3(OR^4)_2$, $OCOR^3$, $OSO_2R^3$, $OCONR^3R^4$, $OCOOR^3$, $CONR^3R^4$, $NR^3R^4$, $NR^3COR^4$, $NR^3COR^4$, $NR^3CONR^4R^5$, NCS, NCO; $R^3$, $R^4$ and $R^5$=alkyl, substituted alkyl, alkenyl, substituted alkenyl, aryl, substituted aryl, or heterocyclic; m=3–8; and n=1–6.

In one embodiment, the functional substituents of N-8 include leaving groups, such as halogens, carboxylate esters or sulfonate esters. Sulfonate esters, such as mesylates, tosylates and triflates (trifluoromethanesulfonates) are particularly useful leaving groups. Other groups may be substituted at this position for the purpose of enhancing or reducing lipophilicity, to permit further chemical modification, or to provide a site for biological transformations, such as alkylation, reduction or oxidation. These groups include esters, amides, ethers, acetals, ketals, carbamates, carbonates, amines, ureas, isothiocyanates, phthalamidoalkyl, (N', N'-dimethyl)acetamido, 2,2-di, ethoxyethyl, carbomethoxymethyl, aryl, substituted aryl, heterocyclic, tetrahydropyran, cycloalkymethyl, and the like.

General Procedure for N-Alkylation of Nor-β-CIT

N-Alkylation reactions are typically carried out with 0.27 mmol of nor-β-CIT (compound 4). To a solution of nor-β-CIT and triethylamine (46 mmol) in absolute EtOH or anhydrous toluene is added the appropriate alkyl bromide (0.4 mmol) and KI (10 mg). The mixture is refluxed under nitrogen from 1 to 24 hours depending on alkyl bromide monitoring by thin layer chromatography (TLC) to the completion of reaction. The solvent is then removed under reduced pressure and the residue is passed through a silica gel column (eluted with hexane/ether/TEA) to yield the pure compounds. Examples 10–14 describe alkylation reactions of the N-8 group.

Example 10

Synthesis of N-phthalamidopropyl-β-CIT

Nor-β-CIT in triethylamine is combined with phthalamidopropyl bromide according to the protocol set forth above. The product, N-phthalamidopropyl-β-CIT, has the following physical characteristics: mp 136°–138° C. (HCl salt); $[α]_D^{20}$–119.8° C. (C, 0.31, MeOH) (free base).

$^1$H NMR (250 MHz, $CDCl_3$) δ 7.83 (m, 2H); 7.70 (m, 2H); 7.55 (d, J=8.4 Hz, 2H); 7.00 (d, J=8.4 Hz, 2H); 3.79 (m, 1H); 3.68 (m, 1H); 3.52 (s, 3H); 3.41 (m, 1H); 2.89 (m, 2H); 2.51 (m, 3H); 2.32 (m, 3H); 2.03 (m, 2H); 1.67 (m, 5H).

MS (FAB, NBA): 559 (27%); 445 (22%); 444 (100%); 417 (27%); Anal. ($C_{26}H_{26}N_2O_4I$•HCl•$H_2O$; Calcd. C, 51.04; H, 4.78; N, 4.58; Found C, 50.99; H, 4.92; N, 4.54.

Example 11

Synthesis of N-((N', N'-dimethyl)acetamido)-β-CIT

Nor-β-CIT in triethylamine is combined with N',N'-dimethylbromoacetamide according to the protocol set forth above. The product, N-((N',N'-dimethyl)acetamido)-β-CIT, has the following physical characteristics: mp 194°–196° C.; $[α]_D^{20}$–45.3° (c, 0.3, MeOH).

$^1$H NMR (250 MHz, $CDCl_3$): δ 7.58 (d, J=8.3Hz, 2H); 7.00 (d, J=8.3 Hz, 2H); 3.70 (m, 1H); 3.45 (s, 3H); 3.12 (m, 1H); 3.11 (m, 2H); 2.90 (s, 3H); 2.55 (m, 1H); 2.18 (m, 2H); 1.65 (m, 4H); Anal. ($C_{19}H_{24}N_2O_3I$); Calcd. C, 50.12; H, 5.31; N, 6.15; Found C, 49.88; H, 5.60; N, 6.04.

Example 12

Synthesis of N-(2,2-dimethoxyethyl-β-CIT

Nor-β-CIT in triethylamine is combined with 2,2,-dimethoxyethyl bromide according to the protocol set forth above. The product, N-(2,2-dimethoxyethyl)-β-CIT, has the following physical characteristics: mp 126°–128 ° C.; $[α]_D^{20}$–36.6° (c, 0.3, MeOH).

$^1$H NMR (250 MHz, $CDCl_3$) δ 7.66 (d, J=8.3 Hz, 2H); 7.02 (d, J=8.3 Hz, 2H); 4.32 (t, J=5.2 Hz, 1H); 4.48 (m, 1H); 3.78 (m, 1H); 3.51 (s, 3H); 3.42 (m, 1H); 3.37 (s, 3H); 3.35 (s, 3H); 2.88 (m, 2H); 2.57 (td, J=2.7 Hz, J=12.1 Hz; 1H); 2.41 (m, 2H); 2.03 (m, 2H); 1.66 (m, 4H).

MS (FAB,NBA): 461 (21%); 460 (100%, M+H$^+$); 459 (2%); 428 (12%); 245 (23%); Anal. ($C_{19}H_{26}NO_4I$); Calcd. C, 49.68; H, 5.71; N, 3.05; Found C, 49.71; H, 5.71; N, 2.99.

Example 13

Synthesis of N-(carbomethoxymethyl)-β-CIT

Nor-β-CIT in triethylamine is combined with carbomethoxymethyl bromide according to the protocol set forth above. The product, N-(carbomethoxymethyl-β-CIT, has the following physical characteristics: mp 120°–122° C.; $[α]_D^{20}$–58.7° (C, 0.3, MeOH).

¹H NMR (250 MHz, CDCl₃) δ: 7.58 (d, J=8.4 Hz, 2H); 7.02 (d, J=8.4 Hz, 2H); 3.74 (m, 1H); 3.68 (s, 3H); 3.51 (s, 3H); 3.58 (s, 3H); 3.45 (m, 1H); 3.14 (dd, J=16.5 Hz, J=13.3 Hz, 2H); 2.90 (m, 2H); 2.75 (t, J=9.8 Hz, 1H); 2.12 (m, 1H); 2.01 (m, 1H); 1.68 (m, 3H).

MS (FAB, NBA): 445 (20%); 444 (100%, M+H⁺); 443 (16%); 412 (5%); 385 (9%); 384 (45%); Anal. ($C_{18}H_{22}NO_4I$); Calcd. C, 48.77; H, 5.00; N, 3.18; Found C, 48.63; H, 5.05; N, 3.12.

Example 14

Synthesis of N-(cyclopropylmethyl)-β-CIT

Nor-β-CIT in triethylamine is combined with cyclopropylmethyl bromide according to the protocol set forth above. The product, N-(cyclopropylmethyl)-β-CIT, has the following physical characteristics: mp 75°–77° C.; $[\alpha]_D^{20}$ –27 6° (c 0 3, MeOH).

¹H NMR (250 MHz, CDCl₃): δ 7.57 (d, J=8.4 Hz, 2H); 7.02 (d, J=8.4 Hz, 2H); 3.95 (m, 1H); 3.59 (s, 3H); 3.43 (m, 1H); 3.58 (s, 3H); 2.90 (m, 2H); 2.55 (dd, J=12.1 Hz, J=2.8 Hz, 1H); 2.39 (dd, J=12.3 Hz, J=5.3 Hz, 1H); 1.96 (m, 3H); 1.64 (m, 4H); 0.78 (m, 1H); 0.43 (m, 2H); 0.06 (m, 2H).

MS (FAB, NBA): 427 (25%); 426 (100%, M+H⁺); 425 (8%); 424 (11%); 300 (8%); Anal. ($C_{19}H_{23}NO_2I$); Calcd. C, 53.78; H, 5.46; N, 3.30; Found C, 53.58; H, 5.67; N, 3.26.

Example 15

Synthesis of 8-(3-chloropropyl)-2β-carbomethoxy-3β-(4'-iodophenyl)-8-azabicyclo-[3.2.1]octane N-(3-Hydroxypropyl)nor-β-CIT (1.8 g, 4.2 mmol) is dissolved in methylene chloride (150 ml) and cooled to 0° C. in an ice-bath under nitrogen. Methanesulfonylchloride (580 mg, 4.4 mmol) is added, followed by addition of 2,6 lutidine (1 mL). The reaction mixture is stirred 2 h and then a second portion of methanesulfonylchloride (580 mg) is added. The mixture is allowed to come to room temperature and stirred for an additional 48 h. The solvent is removed and the residue is chromatographed on silica gel column eluting with ether/hexane/TEA (50/50/5) to give 1.4 g of white solid (top 96°–98° C.).

¹H NMR (300 MHz, CDCl₃): δ 7.58 (d, J=8.4 Hz, 2H); 7.00 (d, 8.4 Hz, 2H); 3.75 (m, 7H); 2.95 (m, 2H); 2.57 (dd, 1H); 2.38 (t, 2H); 1.85 (m, 7H).

MS (FAB, NBA): 495 (19%); 494 (94%); 493 (33%).; 492 (100%); 491 (14%); 490 (7%); 412 (21%); 394 (9%); Anal. $C_{18}H_{23}ClNO_2I$; Calcd. C, 43.99; H, 4.72; N, 2.85; Found C, 44.10; H, 4.80; N, 2.81.

Example 16

Synthesis of 8-(3-bromopropyl)-2β-carbomethoxy-3β-(4'-iodophenyl)-8-azabicyclo-[3.2.1]octane At 0° C., triphenylphosphine (148 mg, 0.55 mmol) is dissolved in methylene chloride, and bromine (88 mg, 0.55 mmol) is added dropwise. After 10 min, N-(3-Hydroxypropyl)nor-β-CIT (215 mg, 0.5 mmol) is slowly added; 30 min later, the solvent is removed at reduced pressure and residue is passed through a silica gel column eluting with ether to give 42 mg of white solid.

¹H NMR (300 MHz, CDCl₃): δ 7.58 (d, J=8.4 Hz, 2H); 7.00 (d, J=8.4 Hz, 2H); 3.75 (m, 7H); 2.95 (m, 2H); 2.57 (dd, 1H); 2.38 (t, 2H); 1.85 (m, 7H).

¹³C NMR (CDCl₃): 171.57; 136.73; 129.33; 90.95; 63.19; 61.16; 52.28; 50.95; 50.17; 45.86; 42.81; 39.26; 33.70; 31.70; 25.79; 8.49.

MS (GC/MS): 447; 384; 346; 257; 217; Anal. ($C_{18}H_{23}BrNO_2I$); Calcd. C, 48.29; H, 5.18; N, 3.13; Found C, 48.39; H, 5.19; N, 3.14.

Example 17

Synthesis of 8-(2-hydroxyethyl)-2β-carbomethoxy-3β-(4'-iodophenyl)-8-azabicyclo-[3.2.1]octane Nor-β-CIT (5 mmol) is dissolved in ethanol (30 mL), together with 2-bromoethyltetrahydropyran (7.5 mmol), triethylamine (0.76 g) and potassium iodide (250 mg). The mixture is heated at reflux under nitrogen for 16 h. When the reaction is completed, the solvent is removed at reduced pressure and the residue is passed through a silica gel column eluting with hexane/ether/triethylamine (15/80/5). The fractions containing product are collected and concentrated to give the pure protected compound. This compound is stirred with H₂O (10 mL), THF (10 ml) and acetic acid (30 mL) during 20 h at 60° C. The solvent is removed, and the residue is basified with NH₄OH and extracted with dichoromethane. The organic layer is dried over MgSO₄ and concentrated. The residue is passed through a silica gel column eluting with hexane/ether/triethylamine (10/80/10). The fractions containing product are collected and concentrated to give 1.3 g of product as a colorless oil.

¹H NMR (300 MHz, CDCl₃): δ 7.58 (d, J=8.4 Hz, 2H); 6.99 (d, J=8.4 Hz, 2H); 3.50 (m, 4H); 3.49 (s, 3H); 2.94 (m, 1H); 2.88 (m, 1H); 2.63 (m, 2H); 2.42 (m, 2H); 2.05 (m, 2H); $[\alpha]_D^{20}$ –34.06° (c, 0.3, MeOH).

Example 18

Synthesis of N-[3-(p-Tolylsulfonyloxyropyl)]-2β-carbomethoxy-3β-(4'-iodopheny)nortropane A solution of N-(3-hydroxypropyl)nor-β-CIT (150 mg, 0.35 mmol), pyridine (100 mg), and p-toluenesulfonyl chloride (100 mg) in chloroform (15 ml) is stirred at room temperature for 4 hr, diluted with water (50 ml), and extracted with chloroform (100 ml). The organic layer is concentrated under reduced pressure. The residue is purified by flash chromatography on silica gel, eluting with hexane/ether/TEA (10/70/0.1) to give 51 mg of product as an oil. The yield is approximately 25%.

¹H NMR (CDCl₃): δ 1.62 –1.80 (m, 3H), 2.01–2.18 (m, 3H), 2.45 (s, 3H), 2.62 (m, 1H), 2.91 (m, 1H), 3.43 (m, 1H), 3.51 (s, 3H), 3.80 (m, 1H), 4.36–4.52 (m, 2H), 6.99–7.58 (ABq, 4H), and 7.55–7.80 (ABq, 4H). Elemental analysis calculated for $C_{25}H_{30}NO_5IS•½H_2O$: C, 50.68; H, 5.27; N, 2.36; Found: C, 50.64; H, 5.45; N, 2.10.

Example 19

Synthesis of N-(2,2-difluoroethyl)-2β-carbomethoxy-3β-(4'-iodopheny)nortropane

A solution of nor-β-CIT (300 mg, 0.8 mmol), 1,1-difluoro-2-trifluoromethanesulfonyloxyethane (300 mg, 1.4 mmol), and triethylamine (1 ml) in acetone (15 ml) is stirred at room temperature overnight. The reaction mixture is filtered and the separated residue washed with toluene (2×2 ml). The combined filtrate and washings are concentrated under reduced pressure. The residue is purified by flash chromatography on silica gel, eluting with hexane/ether/ TEA (10/7/0.1) to give 160 mg of product as a white solid. mp. 113°–114° C.; yield is approximately 46%.

¹H NMR (CDCl₃): δ 1.62–1.80 (m, 3H), 2.01–2.18 (m, 3H), 2.53–2.55 (m, 2H), 2.62 (m, 1H), 2.91 (m, 1H), 3.43 (m, 1H), 3.51 (s, 3H), 3.80 (m, 1H), 4.36–4.52 (m, 1H), 6.99–7.02 and 7.55–7.58 (ABq, 4H). Elemental analysis calculated for $C_{17}H_{20}NO_2IF_2 \cdot \frac{1}{2}H_2O$: C, 45.96; H, 4.77; N, 3.22; Found: C, 46.05; H, 4.72; N, 3.16.

Example 20

Synthesis of N-(3-hydroxypropyl)-2β-carbomethoxy-3β-(4'-iodopheny)tropane

A solution of nor-β-CIT (250 mg, 0.67 mmol), 3-bromopropanol (300 mg, 2.13 mmol) and triethylamine (0.5 ml) in toluene (20 ml) is refluxed under a dry nitrogen atmosphere for 4 hr, cooled and filtered. The separated residue is washed with toluene (2×2 ml). The combined filtrate and washings are concentrated under reduced pressure. The residue was purified by flash chromatography on silica gel, eluting with hexane/ether/TEA (10/7/0.1) to give 168 mg of product as a liquid. Yield is approximately 58%.

$^1$H NMR (CDCl$_3$): δ 1.62–1.80 (m, 5H), 1.98–2.18 (m, 2H), 2.36–2.42 (m, 2H), 2.51–2.63 (m), 2.90–3.02 (m, 2H), 3.40 [s(br), m, 1H], 3.70 [s(br), 1H], 4.44–4.59 (m, 2H), 7.00–7.03 and 7.57–7.60 (ABq, 4H). Elemental analysis calculated for $C_{18}H_{24}NO_3F$: C, 50.36; H, 5.64; N, 3.26; Found: C, 50.35; H, 5.57; N, 3.19.

Example 21

Synthesis of N-[3-(methanesulfonyloxy)propyl]-2β-carbomethoxy-3β-(4'-iodopheny)nortropane To a solution of N-(3-hydroxypropyl)nor-β-CIT (380 mg, 0.88 mmol) and 2,6-lutidine (150 µl) in chloroform (25 ml) is added methanesulfonyl chloride (152 mg, 1.33 mmol) at 0° C. The solution is stirred at 0° C. for 2 hr and then a second portion of methanesulfonyl chloride is added and stirring is continued at room temperature for an additional 4 hr. After removal of the solvent, the residue is purified by flash chromatography on silica gel, eluting with hexane/ether/TEA (10/7/0.1) to give 190 mg of product as an oil. Yield is approximately 40%.

$^1$H NMR (CDCl$_3$): δ 1.62–180 (m, 3H), 2.01–2.18 (m, 3H), 2.45 (s, 3H), 2.62 (m, 1H), 2.91 (m, 1H), 3.04 (s, 3H), 3.43 (m, 1H), 3.51 (s, 3H), 3.80 (m, 1H), 4.36–4.31 (m, 2H) and 6.99–7.58 (ABq, 4H).

Elemental analysis calculated for $C_{19}H_{26}NO_5IS \cdot \frac{1}{2}H_2O$: C, 43.43; H, 5.37; N, 2.67; Found: C, 43.12; H, 5.15; N, 2.58.

Preparation of Radiolabeled Compounds from the Nonradioactive Intermediates

In general, the leaving group attached to the moiety at N-8 is capable of being displaced by a radionuclide such as $^{18}$F. The chemistry of the reaction is based on nucleophilic substitution of [$^{18}$F]fluoride into an activated precursor dissolved in a solvent.

In general, the precursor is an N-substituted β-CIT derivative that includes a leaving group on the moiety attached to N-8. The leaving group is preferably a mesylate, or another sulfonate ester, such as tosylate, triflate, or a halogen (iodide, bromide, chloride), however other leaving groups may also be used. Solvents used in the reaction are preferably anhydrous, polar, aprotic solvents, such as acetonitrile, dimethylsulfoxide, dimethylformamide, N-methylpyrrolidone, hexamethylphosphoric triamide, and the like.

The radioisotope is generated in minute quantities and generally requires an auxilliary reagent to dissolve in the solvent and participate in the chemical reaction. The solubilizing agent can be any agent capable of solubilizing radionuclides that takes the form $M^{+X^-}$. $M^+$ is preferably the complex of potassium and 4,7,13,16,21,24-hexaoxa-1,10-diazabicyclo[8.8.8]hexacosane or an alkali metal ions, such as $Na^+$, $Ce^+$, $Ru^+$, or a tetraalkylammonium, such as tetramethylammonium, or an ion exchange resin functionalized with quaternary amine groups. $X^-$ is preferably carbonate, bicarbonate, hydroxide, or formate. However other counterions may also be used.

Example 22

Preparation of [$^{18}$F]-8-(3-fluoropropyl)-2β-CIT from N-(3-mesyloxypropyl)-N-nor-β-CIT An aqueous solution of [$^{18}$F]fluoride ions (0.5 mL) is mixed with 4,7,13,16,21,24-hexaoxa-1,10-diazabicyclo[8.8.8]hexacosane (10 mg) and potassium carbonate (1 mg) in a borosilicate glass vessel of 5 mL capacity. The vessel is partially immersed in an oil bath thermostated to 100° C., and the solution evaporated to dryness using a stream of nitrogen. An aliquot of anhydrous acetonitrile (1 mL) is added to the reaction vessel and allowed to evaporate under the nitrogen flow. This addition/evaporation step is performed a second time. Heating of the vessel is continued for approximately one minute after evaporation of the second aliquot.

The vessel is next raised above the oil bath. To the residue is added a solution of N-(3-mesyloxypropyl)-N-nor-β-CIT (2 mg; see Example 21) in anhydrous acetonitrile (1 mL). The vessel is re-immersed in the oil bath so that the solvent achieves gentle reflux. Heating is continued for approximately five minutes, and then the vessel is cooled to room temperature.

The reaction mixture is concentrated to near dryness under a stream of nitrogen. The residue is dissolved in 3:1 methanol-water (0.5 mL) and injected into a high pressure liquid chromatograph fitted with a 10×250 mm column packed with octadecyl-functionalized silica and eluted with 3:1 methanol-water at 4 mL/min. The effluent is collected in test tubes at 0.5 minute intervals. The fractions containing N-(3-[$^{18}$F]fluoropropyl)-N-nor-β-CIT are combined, evaporated to dryness, and redissolved in USP sodium chloride injection containing 5% by volume USP ethanol and 0.1 mM L-ascorbic acid.

Other modifications and implementations will occur to those skilled in the art without departing from the spirit and the scope of the invention as claimed. Accordingly, the above-description is not intended to limit the invention except as indicated in the following claims.

What is claimed is:

1. A neuroprobe for mapping monoamine reuptake sites, the neuroprobe having the formula:

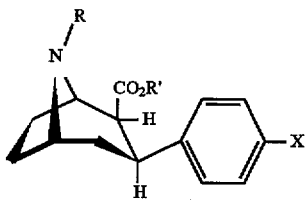

wherein
  $R=(CH_2)_nOSO_2R^3$;
    wherein $R^3$=alkyl, substituted alkyl, alkenyl, substituted alkenyl, aryl, substituted aryl, and heterocyclic; and n=1–6;
  $R'=C_wH_{2w+1}$ wherein w=0–6 and C includes an isotope of carbon; and
  X=an isotope of Cl, an isotope of Br, an isotope of F, an isotope of I, or $Sn(R''_1 R''_2 R''_3)$, wherein $R''_1$=a $C_pH_{2p+1}$ group where p=1–6, or an aryl group;
$R''_2$=a $C_pH_{2p+1}$ group where p=1–6, or an aryl group; and
$R''_3$=a $C_pH_{2p+1}$ group where p=1–6, or an aryl group.

2. The neuroprobe of claim 1, wherein the iodine atom is a radioactive isotope of iodine.

3. The neuroprobe of claim 2, wherein the radioactive isotope of iodine is selected from the group consisting of $^{123}$I, $^{125}$I, and $^{131}$I.

4. The neuroprobe of claim 1, wherein in R', C includes a radioactive isotope of carbon.

5. A kit for preparing a radiolabeled neuroprobe for mapping monoamine reuptake sites, the kit comprising:

a precursor of the formula:

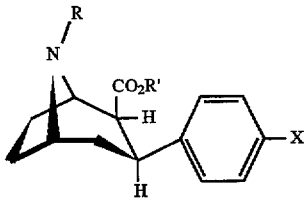

wherein
$R=(CH_2)_nOSO_2R^3$;
wherein $R^3$=alkyl, substituted alkyl, alkenyl, substituted alkenyl, aryl, substituted aryl, and heterocyclic; and n=1–6;
$R'=C_wH_{2w+1}$ wherein w=0–6 and C includes an isotope of carbon; and X=an isotope of Cl, an isotope of Br, an isotope of F, an isotope of I, or Sn ($R''_1 R''_2 R''_3$) wherein $R''_1$=a $C_pH_{2p+1}$ group where p=1–6 or an aryl group;
$R''_2$=a $C_pH_{2p+1}$ group where p=1–6 or an aryl group; and
$R''_3$=a $C_pH_{2p+1}$ group where p=1–6, or an aryl group.

6. The kit of claim 5, wherein said isotope of I is a radioactive isotope of iodine.

7. The kit of claim 6, wherein said isotope of I is selected from the group consisting of $^{123}$I, $^{125}$I, and $^{131}$I.

8. The kit of claim 6, wherein the precursor is reacted in the presence $^{18}$F.

9. The kit of claim 8, wherein the $^{18}$F is selected from the group consisting of Na$^{18}$F, K$^{18}$F, and Cs$^{18}$F.

10. The kit of claim 8, wherein said $^{18}$F is complexed with a reagent of the formula M$^+$X$^-$, wherein:

M$^+$=a complex of 4,7,13,16,21,24-hexaoxa-1,10-diazabicyclo[8.8.8]hexacosane and one of K, Na, Ce, Ru, a tetraalkylammonium ion, and an ion exchange resin functionalized with quaternary amine groups; and X$^-$=carbonate, bicarbonate, hydroxide, and formate.

11. The kit of claim 5, wherein in R', C includes a radioactive isotope of carbon.

* * * * *

UNITED STATES PATENT AND TRADEMARK OFFICE
CERTIFICATE OF CORRECTION

PATENT NO : 5,698,179
DATED : December 16, 1997
INVENTOR(S): John L. Neumeyer, et al.

It is certified that error appears in the above-identified patent and that said Letters Patent is hereby corrected as shown below:

In the Heading, Insert terminal disclaimer as follows:
--[*] Notice: The term of this patent shall not extend beyond the expiration date of Patent Nos. 5,310,912, and 5,439,666.--.

In the Abstract, line 6, "$(CF_.)_nY$," should read --$(CH_2)_nY$,--.

In the Abstract, line 7, "heterocyclic" should read --heterocyclic,--.

In the Abstract, line 21, "$CH_{p+1}$" should read --$C_pH_{2p+1}$--.

Column 3, line 28, "$CO(CF_2)_nY,(CF_.)CHF_.,$" should read --$CO(CH_2)_nY,(CH_2)CHF_2$,--.

Column 3, line 29, "substituted aryl" should read --substituted aryl,--.

Column 3, line 29, "$CH_2H, CO_R^3$," should read --$CO_2H, CO_2R^3$,--.

Column 5, line 2, "Fmol/kg" should read --$\mu$mol/kg--.

UNITED STATES PATENT AND TRADEMARK OFFICE
CERTIFICATE OF CORRECTION

PATENT NO : 5,698,179
DATED : December 16, 1997
INVENTOR(S) : John L. Neumeyer, et al.

It is certified that error appears in the above-identified patent and that said Letters Patent is hereby corrected as shown below:

Column 8, line 64, "of2-beta" should read --of 2-beta--.

Column 11, line 46, "$(CF_2)_n$" should read --$(CH_2)_n$--.

Column 11, line 46, "$(CF_2)_nY$" should read --$(CH_2)_nY$--.

Column 11, line 48, "$CO_2NR_3R^4,OH,$" should read --$CO_2NR^3R^4,OH,OR^3,$--.

Column 11, line 50, "$NR^3COR^4,$" (2nd occurrence) should read ---$NR^3CO_2R^4,$--.

Column 13, line 17, "276°" should read --27.6°--.

Signed and Sealed this

Twenty-eighth Day of December, 1999

Attest:

Attesting Officer

Q. TODD DICKINSON

Acting Commissioner of Patents and Trademarks